(12) United States Patent
Flower

(10) Patent No.: US 10,856,753 B2
(45) Date of Patent: Dec. 8, 2020

(54) CENTRAL CAVITY PERFUSION CALCULATION

(71) Applicant: KONINKLIJKE PHILIPS N.V., Eindhoven (NL)

(72) Inventor: Abigail Acton Flower, Mahopac, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 717 days.

(21) Appl. No.: 15/300,318

(22) PCT Filed: Mar. 27, 2015

(86) PCT No.: PCT/IB2015/052260
§ 371 (c)(1),
(2) Date: Sep. 29, 2016

(87) PCT Pub. No.: WO2015/150998
PCT Pub. Date: Oct. 8, 2015

(65) Prior Publication Data
US 2017/0181647 A1 Jun. 29, 2017

Related U.S. Application Data

(60) Provisional application No. 61/973,391, filed on Apr. 1, 2014.

(51) Int. Cl.
*A61B 5/0295* (2006.01)
*A61B 5/02* (2006.01)
(Continued)

(52) U.S. Cl.
CPC ......... *A61B 5/0295* (2013.01); *A61B 5/029* (2013.01); *A61B 5/02028* (2013.01); *A61B 5/7257* (2013.01); *A61B 5/7278* (2013.01)

(58) Field of Classification Search
CPC .............. A61B 5/02953; A61B 5/0295; A61B 5/02028; A61B 5/029; A61B 5/7257; A61B 5/7278; A61B 5/7203
See application file for complete search history.

(56) References Cited

U.S. PATENT DOCUMENTS 3,909,792 A * 9/1975 Harris .................. A61B 5/0432 345/440
4,781,201 A * 11/1988 Wright ................. A61B 5/0205 600/484
(Continued)

FOREIGN PATENT DOCUMENTS

| JP | 2001017403 A | 1/2001 |
|---|---|---|
| JP | 2009532072 A | 9/2009 |

(Continued)

OTHER PUBLICATIONS

Lee, et al., "A new algorithm for detecting central apnea in neonates", Physiological Measurement, vol. 33, 2012, pp. 1-17.

*Primary Examiner* — Meredith Weare

(57) ABSTRACT

A system, method and non-transitory computer readable storage medium for monitoring a perfusion of a patient. The system, method and computer readable storage medium receive an indication of a voltage applied across a chest of the patient via a first electrode, receive a measurement of a current across the chest of the patient, resulting from the applied voltage via a second electrode, generate an impedance-based respiratory rate waveform based on the applied voltage and the measured current, generate a Fourier Transform of the respiratory rate waveform relative to a heartbeat of the patient, isolate cardiac artifacts in the Fourier Transform and generate a perfusion waveform indicating a perfusion of a chest cavity of the patient based on the isolated cardiac artifacts.

20 Claims, 5 Drawing Sheets

(51) Int. Cl.
*A61B 5/029* (2006.01)
*A61B 5/00* (2006.01)

(56) References Cited

U.S. PATENT DOCUMENTS

| | | |
|---|---|---|
| 5,178,154 A | 1/1993 | Ackmann et al. |
| 5,685,316 A | 11/1997 | Schookin et al. |
| 6,348,038 B1 | 2/2002 | Band et al. |
| 2005/0065554 A1 | 3/2005 | KenKnight et al. |
| 2008/0234594 A1 | 9/2008 | Brooks et al. |
| 2009/0216140 A1* | 8/2009 | Skrabal ............ A61B 5/02028 600/509 |
| 2009/0275855 A1 | 11/2009 | Zielinski et al. |
| 2012/0172730 A1 | 7/2012 | Delos et al. |
| 2013/0281805 A1 | 10/2013 | Mason et al. |

FOREIGN PATENT DOCUMENTS

| | | |
|---|---|---|
| WO | 9737591 A1 | 10/1997 |
| WO | 2007052108 A3 | 5/2007 |
| WO | 2013013153 A1 | 1/2013 |

* cited by examiner

CENTRAL CAVITY PERFUSION CALCULATION

BACKGROUND

Perfusion of the central cavity (e.g., thorax) and changes in this perfusion in a patient is highly useful information in evaluating the cardiovascular state of a patient. There have been numerous attempts at quantifying the perfusion of the central cavity. However, existing systems and methods for quantifying the perfusion of the central cavity are inefficient, cumbersome and/or invasive. For example, a thoracic electrical impedance method requires the placement of extra sensors along with straps/cables on the patient. A Doppler flowmetry method may also be used to quantify the perfusion of the central cavity, but does not provide a continuous measurement, as the equipment if bulky, expensive, and requires hands-on use by a clinician. One can also use central venous pressure (CVP) measurements to calculate perfusion and cardiac output information, but this involves the use of an invasive catheter.

DETAILED DESCRIPTION

The exemplary embodiments include a method for monitoring a perfusion of a patient. The method includes receiving an indication of a voltage applied across a chest of the patient via a first electrode, receiving a measurement of a current across the chest of the patient resulting from the applied voltage via a second electrode, generating an impedance-based respiratory rate waveform based on the applied voltage and the measured current, generating a Fourier Transform of the respiratory rate waveform relative to a heartbeat of the patient, isolating cardiac artifacts in the Fourier Transform and generating a perfusion waveform indicating a perfusion of a chest cavity of the patient based on the isolated cardiac artifacts.

The exemplary embodiments also include a system for monitoring a perfusion of a patient. The system includes a first electrode applying a voltage across a chest of the patient, a second electrode measuring a current across the chest of the patient resulting from the applied voltage and a processor generating an impedance-based respiratory rate waveform based on the applied voltage and the measured current, generating a Fourier Transform of the respiratory rate waveform relative to a heartbeat of the patient, isolating cardiac artifacts in the Fourier Transform and generating a perfusion waveform indicating a perfusion of a chest cavity of the patient based on the isolated cardiac artifacts.

The exemplary embodiments further include a non-transitory computer-readable storage medium including a set of instructions executable by a processor. The set of instructions, when executed by the processor, cause the processor to perform operations, including receiving an indication of a voltage applied across a chest of the patient via a first electrode, receiving a measurement of a current across the chest of the patient resulting from the applied voltage via a second electrode, generating an impedance-based respiratory rate waveform based on the applied voltage and the measured current, generating a Fourier Transform of the respiratory rate waveform relative to a heartbeat of the patient, isolating cardiac artifacts in the Fourier Transform; and generating a perfusion waveform indicating a perfusion of a chest cavity of the patient based on the isolated cardiac artifacts.

Figure 1:
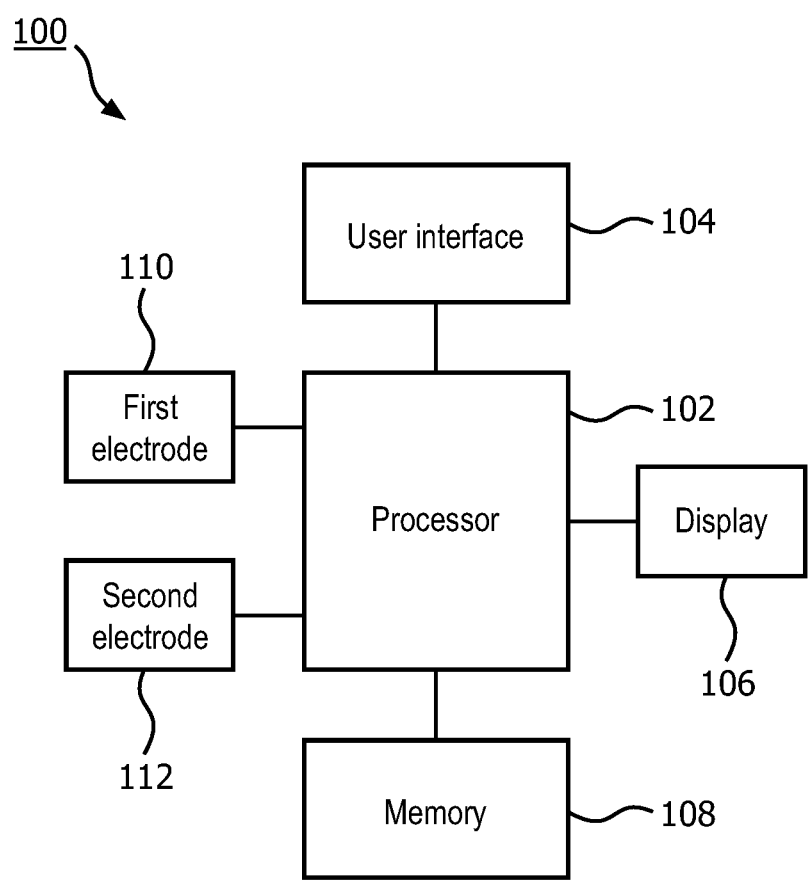
FIG. 1 shows a schematic drawing of a system according to an exemplary embodiment of the present invention.

The exemplary embodiments may be further understood with reference to the following description and the appended drawings, wherein like elements are referred to with the same reference numerals. The exemplary embodiments relate to a system and method for assessing the cardiovascular state of a patient. In particular, the exemplary embodiments describe quantifying a perfusion of the central cavity of the patient to determine the cardiovascular state of the patient. Although exemplary embodiments show and describe using electrodes to determine a respiratory rate of a patient, it will be understood by those of skill in the art that the system and method of the present invention may utilize other devices for determining the respiratory rate such as, for example, As shown in FIG. 1, a system 100 according to an exemplary embodiment of the present disclosure measures a perfusion of a central cavity of a patient. The system 100 comprises a processor 102, a user interface 104, a display 106 and a memory 108. The system 100 also comprises a first electrode 110 and a second electrode 112, each of which are connected (directly or indirectly) to the processor 102 so that a voltage applied by the first electrode 110 and a current measured by the second electrode 112 can be detected and monitored via the processor 102. The first and second electrode 110, 112 may be adhered to a chest of a patient and controlled via the user interface 104 which may include, for example, input devices such as a keyboard, a mouse and/or a touch display on the display 106. The first electrode 110 may be an EKG electrode that applies a small, high frequency voltage across the chest and the second electrode 112 may be a second EKG electrode measuring a resulting current across the chest. Impedance-based respiratory rate measurement is based on the fact that the chest impedance changes with the inspiration and exhalation of air. Since air is a poor conductor, the thorax becomes less conductive as air enters the lungs. This is reflected by an increased impedance across the chest as air is exhaled. Once the voltage is applied and the resulting current across the chest is measured, the processor 102 calculates the impedance by dividing the voltage across the chest with the resulting current. The first and second electrodes 110, 112 may continuously apply a voltage and measure the resulting current, respectively, so that the processor 102 determines the continuous respiratory rate of the patient. Basic impedance is on the order of several hundred ohms, which is relatively stationary, and the respiratory impedance is around, for example, 2 ohms. Another detectable oscillating impedance, however, is that caused by blood being pumped into and out of the thorax by the heart. This impedance change is on the order of half an ohm. This impedance is observable particularly when lungs are emptied after an exhalation. This information may be used to estimate the amount of blood entering the central cavity.

In particular, the processor 102 takes a continuous respiratory waveform and resamples it over a new time domain, for which the heart is the clock and for which the distance between any two heartbeats is equivalent. The information about heartbeats is collected by the associated EKG. The respiratory signal is then interpolated over this new heartbeat-based time domain. At this point, the processor 102 takes the Fourier transform of the respiratory rate waveform of the patient, the x-axis being 1/Heartbeat rather than 1/s. The result is a transform that highlights the cardiac artifact measured by the impedance—e.g., the impedance across the chest caused by blood being pumped into and out of the thorax. The processor 102 then isolates the cardiac artifacts and inverts the Fourier transform of the cardiac artifacts to generate a waveform representing an amount of blood being pumped into and out of the thorax. This new signal is resampled back into the original time via interpolation. Changes in amplitude of the resulting waveform may be analyzed to determine the perfusion of the chest cavity, giving clinicians an idea of the hemodynamic state of the patient. The resulting perfusion waveform may be displayed on the display 106. It will be understood that the resulting perfusion waveform along with any associated data such as the continuous respiratory rate and Fourier transforms may be stored to the memory 108.

Figure 2:
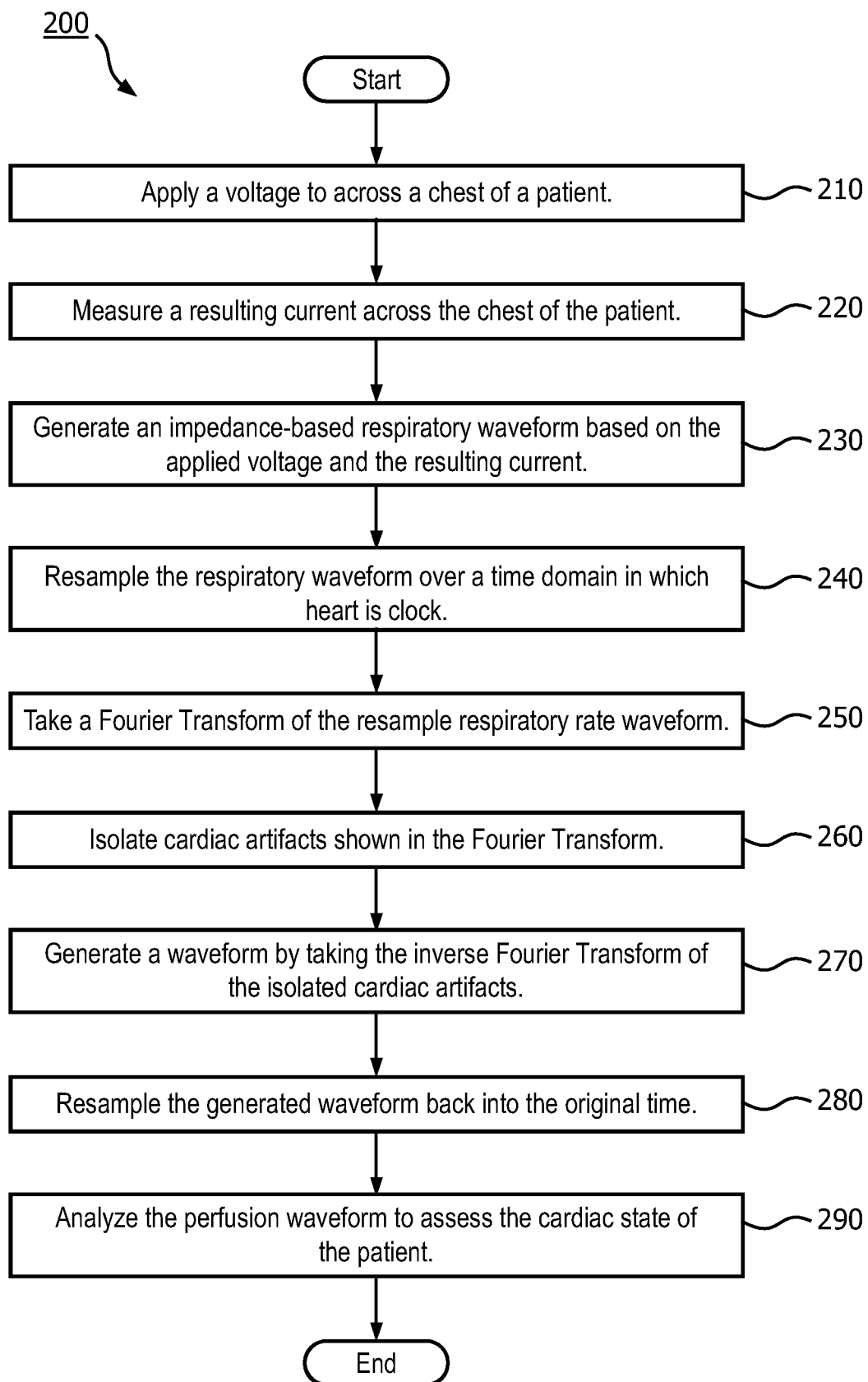
FIG. 2 shows a flow diagram of a method according to an exemplary embodiment of the present invention.
Figure 3:
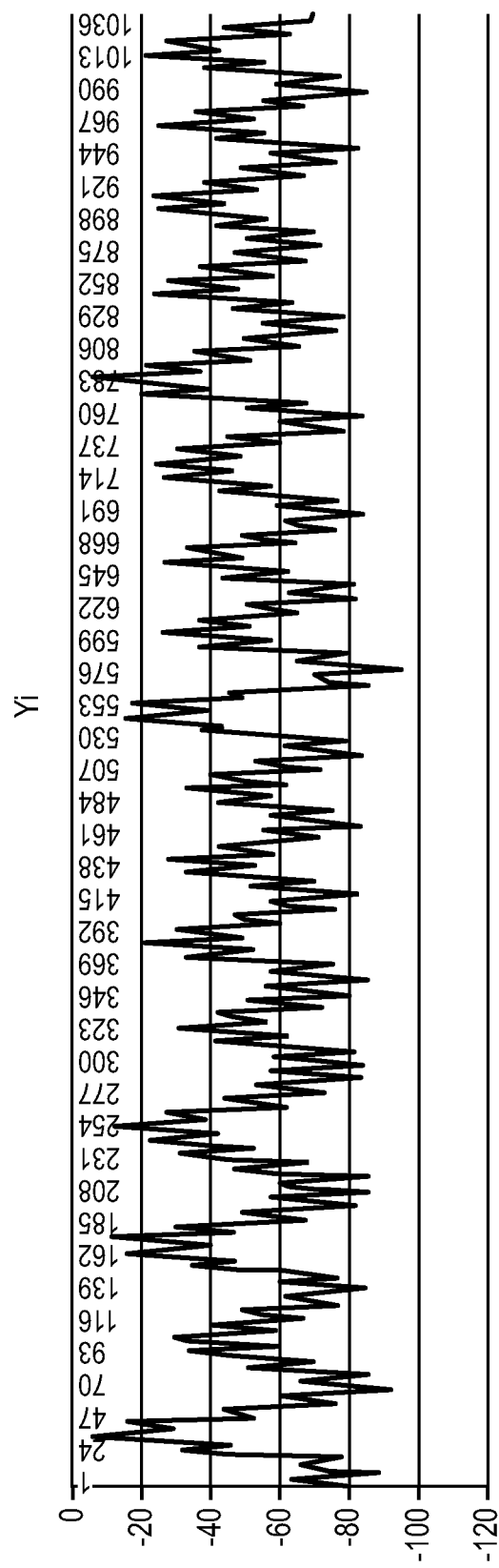
FIG. 3 shows a graph of an exemplary impedance-based respiratory rate waveform of a patient.
Figure 4:
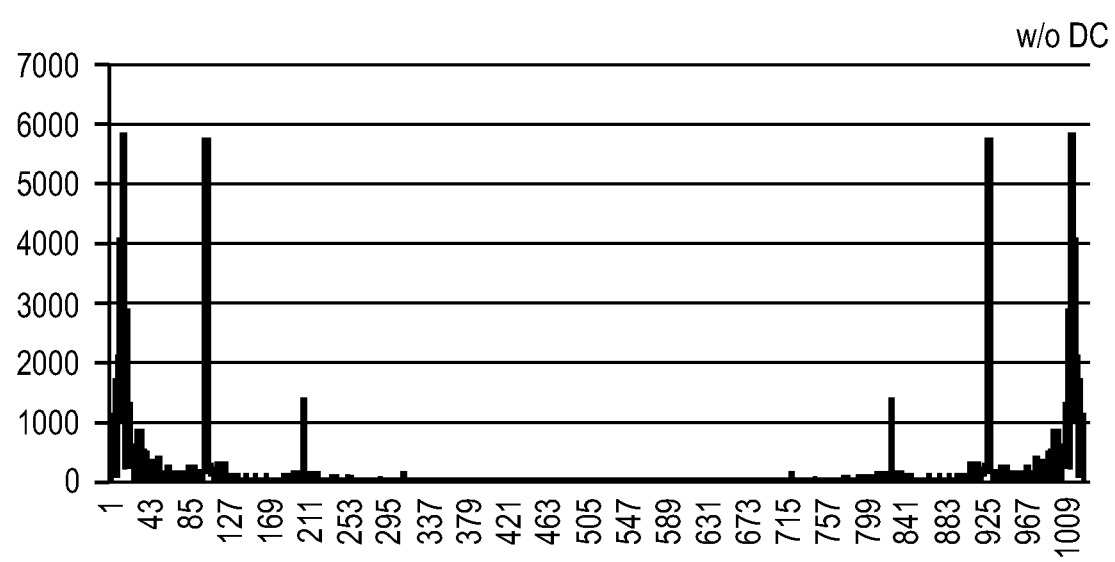
FIG. 4 shows an exemplary Fourier transform of the respiratory rate waveform of FIG. 3.

FIG. 2 shows an exemplary method by which the system 100 generates a waveform representing the perfusion of a patient, for analysis. As discussed above in regard to the system 100, the first and second electrodes 110, 112 are adhered to a chest of the patient. The first and second electrodes 110, 112 may be positioned along the chest and adhered thereto in a manner known to those of skill in the art. In a step 210, the first electrode 110 applies a continuous small, high frequency voltage across the chest of the patient. In a step 220, the second electrode 210, measures the current across the chest of the patient resulting from the applied voltage. The applied voltage and the measured current may be monitored by the processor 102 such that, in a step 230, the processor 102 generates a impedance-based respiratory rate waveform resulting from dividing the applied voltage by the resulting current as shown, for example, in FIG. 3. This respiratory rate waveform may be stored to the memory 108 and/or displayed on the display 106. In a step 240, the processor 102 takes the respiratory rate waveform and resamples it in a new time domain in which the heart acts as the clock. A distance between two heartbeats may be equivalent. The respiratory signal is then interpolated over this new heartbeat-based time domain. In a step 250, the processor 102 then takes the Fourier Transform of the resampled respiratory rate waveform, the x-axis being 1/Heartbeat rather than 1/s, for example, in FIG. 4. In particular, the Fourier Transform may be stretched and/or condensed over time so that each patient heartbeat is equally spaced from one another. It will be understood by those of skill in the art that the DC component may also be removed to normalize the signal shown in Fourier Transform. Cardiac artifacts may be shown in the Fourier Transform as narrow spikes at the frequency of one heartbeat.

Figure 5:
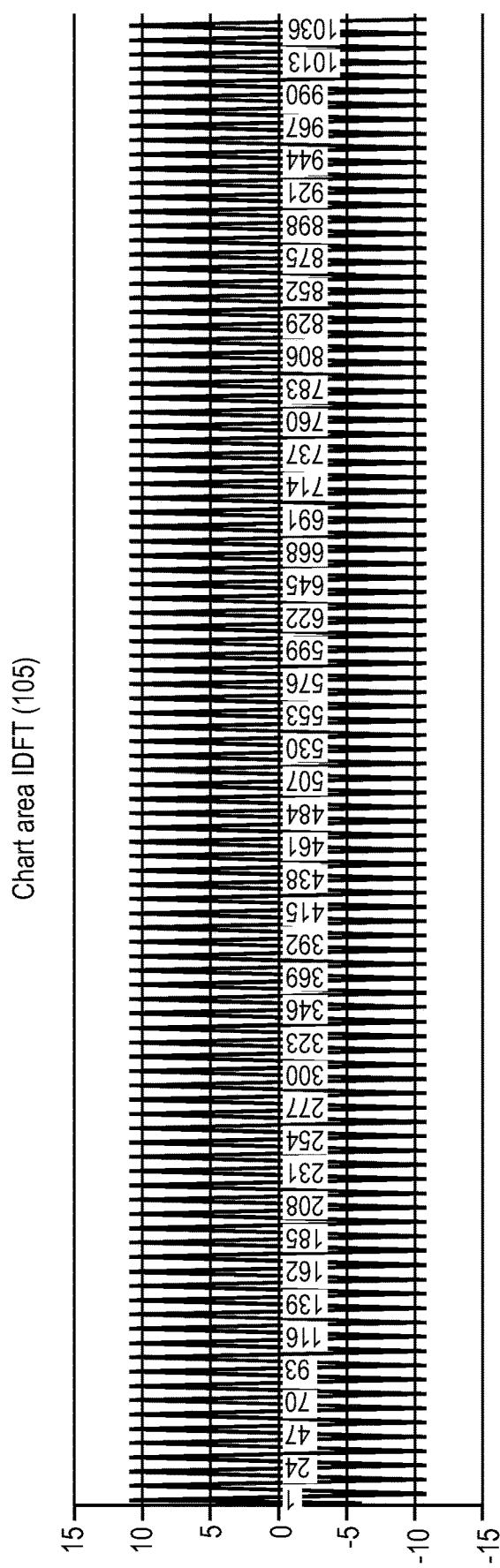
FIG. 5 shows a graph of an exemplary perfusion waveform based on cardiac artifacts identified via the Fourier Transform of FIG. 4.

In a step 260, the cardiac artifacts may be isolated, removing other unnecessary signals resulting from, for example, a movement and breathing of the patient. In a step 270, the processor 102 may take the inverse Fourier Transform of these isolated cardiac artifacts to generate a waveform representing an amount of blood being pumped into and out of the chest cavity, as shown, for example in FIG. 5. In a step 280, the inverse Fourier Transform is resampled back into the original time via interpolation to generate a perfusion waveform. This perfusion waveform may be stored to the memory 108 and/or displayed on the display 106. The perfusion waveform may be analyzed, in a step 290, to determine a cardiac state of the patient. Changes in an amplitude of the perfusion waveform indicate changes in the amount of blood being circulated in the chest cavity and is a good indicator of how the patient's body is handling its blood supply and how well perfused the patient's body is. For example, a decrease in amplitude over time may indicate that the patient is not well perfused and may have hypotension. Thus, analysis of the perfusion waveform may include determining changes in amplitude of the perfusion waveform. When, for example, a decrease in amplitude exceeds a predetermined threshold value or is within a predetermined range of values, the processor 102 may generate a warning to a user (e.g., the clinician) indicating that the patient is not well perfused and may be experiencing hypotension. The warning may be auditory and/or may be displayed on the display 106. It will be understood by those of skill in the art that the predetermined threshold values and predetermined range in values may be changed or updated by a user of the system via the user interface 104. It will also be understood by those of skill in the art that the perfusion waveform may be analyzed along with other available information such as, for example, the amount of blood in peripheral sites of the patient's body, as measured by photoplethysmography, to better understand the hemodynamic state of the patient's body.

It will be understood by those of skill in the art that the perfusion waveform may be generated for a given period of time or may be a continuous waveform generated for as long as the first and second electrodes 110, 112 are applying voltage and measuring current, respectively. Each heartbeat may include a number of amplitudes so that it may be beneficial to be able to view the perfusion waveform in smaller increments of time. For example, the user may be able to select a window or frame, via the user interface 104, which may be moved over portions of the perfusion waveform to better view changes of amplitude within a smaller window of time.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example, generation of the perfusion waveform may be implanted by programs containing lines of code that, when compiled, may be executed on a processor.

It will be apparent to those skilled in the art that various modifications may be made to the disclosed exemplary embodiment and methods and alternatives without departing from the spirit or scope of the disclosure. Thus, it is intended that the present disclosure cover the modifications and variations provided that they come within the scope of the appended claims and their equivalents.

What is claimed is:

1. A method for monitoring a perfusion of a patient, comprising:
    receiving, with a processor, an indication of a voltage applied across a chest of the patient via a first electrode;
    receiving, with the processor, a measurement of a current across the chest of the patient resulting from the applied voltage via a second electrode;

generating, with the processor, an impedance-based respiratory rate waveform based on the applied voltage and the measured current;

generating, with the processor, a Fourier Transform in a heartbeat-based time domain of the impedance-based respiratory rate waveform by using a heartbeat of the patient as a clock;

isolating, with the processor, cardiac artifacts in the Fourier Transform; and generating, with the processor, a perfusion waveform indicating a perfusion of a chest cavity of the patient based on the isolated cardiac artifacts.

2. The method of claim 1, further comprising:
analyzing, with the processor, the perfusion waveform by identifying changes in amplitude to assess a cardiac state of the patient.

3. The method of claim 2, wherein analyzing the perfusion waveform further comprises:
identifying, with the processor, a decrease in the amplitude.

4. The method of claim 3, further comprising:
initiating, with the processor, a warning signal to a user when the decrease in amplitude exceeds a predetermined threshold value.

5. The method of claim 4, wherein the warning signal is one of an auditory signal and a visual signal.

6. The method of claim 1, wherein generating the Fourier Transform further comprises:
removing, with the processor, a DC component.

7. The method of claim 1, wherein generating the perfusion waveform further comprises:
taking, with the processor, an inverse Fourier Transform of the isolated cardiac artifacts.

8. The method of claim 1, further comprising:
storing, with the processor, one of the impedance-based respiratory rate waveform and the perfusion waveform in a memory.

9. The method of claim 1, further comprising:
displaying, with the processor, the perfusion waveform.

10. The method of claim 9, further comprising:
selecting, with a user interface, a portion of the displayed perfusion waveform to view the portion of the perfusion waveform within a predetermined window of time.

11. A system for monitoring a perfusion of a patient, comprising:
a first electrode configured to apply a voltage across a chest of the patient;
a second electrode configured to measure a current across the chest of the patient resulting from the applied voltage;
a processor configured to generate an impedance-based respiratory rate waveform based on the applied voltage and the measured current, generate a Fourier Transform in a heartbeat-based time domain of the impedance-based respiratory rate waveform by using a heartbeat of the patient as a clock, isolate cardiac artifacts in the Fourier Transform, and generate a perfusion waveform indicating a perfusion of a chest cavity of the patient based on the isolated cardiac artifacts.

12. The system of claim 11, wherein the processor is configured to analyze the perfusion waveform by identifying changes in amplitude to assess a cardiac state of the patient.

13. The system of claim 12, wherein the processor is further configured to analyze the perfusion waveform by identifying a decrease in the amplitude.

14. The system of claim 13, wherein the processor is further configured to initiate a warning signal to a user when the decrease in amplitude exceeds a predetermined threshold value.

15. The system of claim 11, wherein the processor is further configured to generate the Fourier Transform by removing a DC component.

16. The system of claim 11, wherein the processor is further configured to generate the perfusion waveform by taking an inverse Fourier Transform of the isolated cardiac artifacts.

17. The system of claim 11, further comprising:
a memory configured to store one of the impedance-based respiratory rate waveform and the perfusion waveform.

18. The system of claim 11, further comprising:
a display configured to display the perfusion waveform.

19. The system of claim 18, further comprising:
a user interface configured to permit a user to select a portion of the displayed perfusion waveform to view the portion the perfusion waveform within a predetermined window of time.

20. A non-transitory computer-readable storage medium including a set of instructions executable by a processor, the set of instructions, when executed by the processor, causing the processor to perform operations, the non-transitory computer-readable storage medium comprising:
instructions for receiving an indication of a voltage applied across a chest of the patient via a first electrode;
instructions for receiving a measurement of a current across the chest of the patient resulting from the applied voltage via a second electrode;
instructions for generating an impedance-based respiratory rate waveform based on the applied voltage and the measured current;
instructions for generating a Fourier Transform in a heartbeat-based time domain of the impedance-based respiratory rate waveform by using a heartbeat of the patient as a clock;
instructions for isolating cardiac artifacts in the Fourier Transform; and
instructions for generating a perfusion waveform indicating a perfusion of a chest cavity of the patient based on the isolated cardiac artifacts.

* * * * *